US009565996B2

(12) United States Patent
Berkner et al.

(10) Patent No.: US 9,565,996 B2
(45) Date of Patent: Feb. 14, 2017

(54) PLENOPTIC OTOSCOPE

(71) Applicants: Kathrin Berkner, Los Altos, CA (US); Sapna A. Shroff, Menlo Park, CA (US); Lingfei Meng, Redwood City, CA (US); Nikhil Balram, Mountain View, CA (US)

(72) Inventors: Kathrin Berkner, Los Altos, CA (US); Sapna A. Shroff, Menlo Park, CA (US); Lingfei Meng, Redwood City, CA (US); Nikhil Balram, Mountain View, CA (US)

(73) Assignee: Ricoh Company, Ltd., Tokyo (JP)

( * ) Notice: Subject to any disclaimer, the term of this patent is extended or adjusted under 35 U.S.C. 154(b) by 549 days.

(21) Appl. No.: 13/896,924

(22) Filed: May 17, 2013

(65) Prior Publication Data

US 2014/0206979 A1 Jul. 24, 2014

Related U.S. Application Data

(60) Provisional application No. 61/754,327, filed on Jan. 18, 2013.

(51) Int. Cl.
*A61B 1/227* (2006.01)
*A61B 5/00* (2006.01)
*A61B 1/00* (2006.01)

(52) U.S. Cl.
CPC ............ *A61B 1/227* (2013.01); *A61B 1/00186* (2013.01); *A61B 1/00009* (2013.01); *A61B 5/0062* (2013.01); *A61B 5/0082* (2013.01)

(58) Field of Classification Search
CPC ... A61B 5/6817; A61B 5/0075; A61B 5/0062; A61B 5/0082; A61B 1/227; A61B 1/00186; A61B 1/00009
See application file for complete search history.

(56) References Cited

U.S. PATENT DOCUMENTS 6,110,106 A * 8/2000 MacKinnon et al. ........ 600/181
6,483,535 B1 11/2002 Tamburrino et al.
(Continued)

FOREIGN PATENT DOCUMENTS

CN 1531410 A 9/2004
CN 101305899 A 11/2008
(Continued)

OTHER PUBLICATIONS

Levoy et al, "Light Field Microscopy." ACM Transactions on Graphics 25(3) 2006, pp. 1-11.*
(Continued)

*Primary Examiner* — Long V Le
*Assistant Examiner* — Angela M Hoffa
(74) *Attorney, Agent, or Firm* — Fenwick & West LLP (57) ABSTRACT

A plenoptic otoscope enables three-dimensional and/or spectral imaging of the inside of the ear to assist in improved diagnosis of inflammations and infections. The plenoptic otoscope includes a primary imaging system and a plenoptic sensor. The primary imaging system includes an otoscope objective and relay optics, which cooperate to form an image of an inside of an ear at an intermediate image plane. The plenoptic sensor includes a microimaging array positioned at the intermediate image plane and a sensor array positioned at a conjugate of the pupil plane. An optional filter module may be positioned at the pupil plane or one of its conjugates to facilitate three-dimensional and/or spectral imaging.

17 Claims, 6 Drawing Sheets

(56) References Cited

U.S. PATENT DOCUMENTS

| | | | |
|---|---|---|---|
| 7,058,441 B2 | 6/2006 | Sharar et al. | |
| 7,399,375 B2 | 7/2008 | Leiser et al. | |
| 7,433,042 B1 | 10/2008 | Cavanaugh et al. | |
| 7,448,753 B1* | 11/2008 | Chinnock | 351/206 |
| 7,544,163 B2* | 6/2009 | MacKinnon et al. | 600/178 |
| 7,723,662 B2 | 5/2010 | Levoy et al. | |
| 7,901,351 B2 | 3/2011 | Prescott | |
| 7,936,392 B2 | 5/2011 | Ng et al. | |
| 8,066,634 B2 | 11/2011 | Andreassen et al. | |
| 8,100,826 B2* | 1/2012 | Mackinnon et al. | 600/178 |
| 8,107,086 B2 | 1/2012 | Hart | |
| 8,143,565 B2 | 3/2012 | Berkner et al. | |
| 8,944,596 B2* | 2/2015 | Wood et al. | 351/206 |
| 8,949,078 B2 | 2/2015 | Berkner et al. | |
| 9,392,933 B2* | 7/2016 | Bedard | A61B 1/227 |
| 2004/0147810 A1 | 7/2004 | Mizuno | |
| 2005/0228231 A1* | 10/2005 | MacKinnon et al. | 600/180 |
| 2005/0283065 A1 | 12/2005 | Babayoff | |
| 2008/0259274 A1* | 10/2008 | Chinnock | 351/206 |
| 2010/0004513 A1* | 1/2010 | Mackinnon et al. | 600/180 |
| 2011/0026037 A1 | 2/2011 | Forster et al. | |
| 2011/0152621 A1 | 6/2011 | Magalhaes Mendes et al. | |
| 2012/0065473 A1 | 3/2012 | Andreassen et al. | |
| 2012/0182438 A1 | 7/2012 | Berkner et al. | |
| 2012/0226480 A1 | 9/2012 | Berkner et al. | |
| 2012/0320340 A1* | 12/2012 | Coleman, III | 351/208 |
| 2012/0327426 A1* | 12/2012 | Hart et al. | 356/601 |
| 2012/0327427 A1* | 12/2012 | Hart et al. | 356/601 |
| 2013/0002426 A1* | 1/2013 | Hart et al. | 340/540 |
| 2013/0002824 A1* | 1/2013 | Hart et al. | 348/46 |
| 2013/0003078 A1* | 1/2013 | Hart et al. | 356/601 |
| 2013/0027516 A1* | 1/2013 | Hart et al. | 348/45 |
| 2013/0128223 A1* | 5/2013 | Wood et al. | 351/206 |
| 2013/0289353 A1* | 10/2013 | Seth et al. | 600/200 |
| 2014/0012141 A1* | 1/2014 | Kim et al. | 600/476 |
| 2014/0192255 A1 | 7/2014 | Shroff et al. | |
| 2014/0316238 A1* | 10/2014 | Berkner et al. | 600/407 |
| 2014/0350379 A1* | 11/2014 | Verdooner | 600/407 |
| 2015/0005640 A1* | 1/2015 | Davis et al. | 600/476 |
| 2015/0005644 A1* | 1/2015 | Rhoads | 600/477 |
| 2015/0116526 A1* | 4/2015 | Meng et al. | 348/218.1 |
| 2015/0126810 A1* | 5/2015 | Wood et al. | 600/200 |

FOREIGN PATENT DOCUMENTS

| | | |
|---|---|---|
| CN | 102105780 A | 6/2011 |
| CN | 102265124 A | 11/2011 |
| JP | 2001-157664 A | 6/2001 |
| JP | 2002-34916 A | 2/2002 |
| WO | WO 2012/058641 A2 | 5/2012 |

OTHER PUBLICATIONS

Berkner et al, "Measuring color and shape characteristics of objects from light fields." Imaging and Applied Optics, 2015, 3 pages.*
N. Bedard, I. Tošić, L. Meng, A. Hoberman, J. Kovačević, and K. Berkner, "In Vivo Middle Ear Imaging with a Light Field Otoscope," in Optics in the Life Sciences, OSA Technical Digest (online) (Optical Society of America, 2015), paper BW3A.3.*
Ng et al, "Light Field Photography with a Hand-held Plenoptic Camera," Standford Tech Report, (2005), pp. 1-11.*
N. Bedard, I. Tosic, L. Meng, and K. Berkner, "Light Field Otoscope," in Imaging and Applied Optics 2014, OSA Technical Digest (online) (Optical Society of America, 2014), paper IM3C.6.*
Chinese Office Action, Chinese Application No. 201410010071.X, May 6, 2015, 7 pages (with concise explanation of relevance).
United States Office Action, U.S. Appl. No. 14/318,578, filed Dec. 10, 2015, 13 pages.

* cited by examiner

PLENOPTIC OTOSCOPE

CROSS-REFERENCE TO RELATED APPLICATION

This application claims priority under 35 U.S.C. §119(e) to U.S. Provisional Patent Application Ser. No. 61/754,327, titled "Plenoptic Otoscope," filed Jan. 18, 2013. The subject matter of the foregoing is incorporated herein by reference in its entirety.

BACKGROUND OF THE INVENTION

1. Field of the Invention

This invention relates generally to otoscopes for imaging the inside of human or animal ears.

2. Description of the Related Art

Imaging inside of the human or animal ear is a common task for doctors. Typically a doctor uses an otoscope to look inside the ear of the patient. Such exam is common procedure when trying to diagnose ear infections. Most doctors use a manual otoscope, which is simply a magnifier combined with an illuminator. The image that the doctor sees exists only in the doctor's memory. Therefore, comparing different images looked at different times is difficult and not objective.

There exist digital otoscopes that have a digital camera embedded in the otoscope or at the end of a fiber-optic cable that guides the light from the instrument head to an external module. The digital data are then viewed on an external display. Such digital otoscopes are marketed as solutions for telemedicine applications. Cameras currently used in digital otoscope consist of conventional imaging optics and sensors. With the rapid development of mobile platforms for smart healthcare applications, attachments for cell phones are being developed that allow the imaging of the inside of an ear with a smartphone for illumination, image capture, and display.

The features that doctors analyze when trying to make a diagnosis for ear inflammation ("otitis media") include features such as bulging of the ear drum, translucency, and yellowness of tissue. However, these features are difficult to analyze from flat two-dimensional images taken by conventional cameras.

Therefore, there exists a need for improved data acquisition to allow the extraction of three dimensions and color features more reliably.

SUMMARY OF THE INVENTION

The present invention overcomes the limitations of the prior art by providing a plenoptic otoscope. A plenoptic otoscope can be designed to provide good quality data for feature extraction for otitis diagnosis. In one implementation, a plenoptic sensor and an optional filter module are combined with a conventional digital otoscope to create a plenoptic otoscope. With these additions, three-dimensional (3D) shapes, translucency and/or color information can be captured.

In one embodiment, a plenoptic otoscope includes a primary imaging system and a plenoptic sensor. The primary imaging system is characterized by a pupil plane, and includes an otoscope objective and relay optics, which cooperate to form an image of the inside of an ear at an intermediate image plane. The plenoptic sensor includes a microimaging array positioned at the intermediate image plane and a sensor array positioned at a conjugate of the pupil plane.

In one implementation, a plenoptic otoscope further includes a filter module positioned at a pupil plane conjugate (i.e., at the pupil plane or one of its conjugates). In one approach, the filter module is located in a detachable tip, and is positioned at an entrance pupil of the primary imaging system when the detachable tip is attached to the otoscope. In this way, different filter modules can be included in detachable tips, and the filter modules can be switched in and out of the plenoptic otoscope by switching detachable tips.

In another implementation, a plenoptic otoscope is operable in a depth imaging mode. In the depth imaging mode, a plenoptic image captured by the sensor array is processed to provide a three-dimensional depth image of an inside of an ear. Alternately or additionally, a plenoptic otoscope is operable in a spectral imaging mode. In the spectral imaging mode, a plenoptic image captured by the sensor array is processed to provide two or more different spectral images of an inside of an ear. The plenoptic otoscope may be switchable between the depth imaging mode and the spectral imaging mode.

Other aspects of the invention include methods, devices, systems, and applications related to the approaches described above and its variants.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed. To facilitate understanding, identical reference numerals have been used where possible, to designate identical elements that are common to the figures.

A plenoptic otoscope design can overcome the poor data quality of current otoscopes for feature extraction for otitis diagnosis. In one implementation, a plenoptic sensor is added to a conventional digital otoscope as well as an optional filter module inside the otoscopic instrument. With these additions, three-dimensional (3D) shapes, translucency, and/or detailed color information can be captured.

Figure 1A:
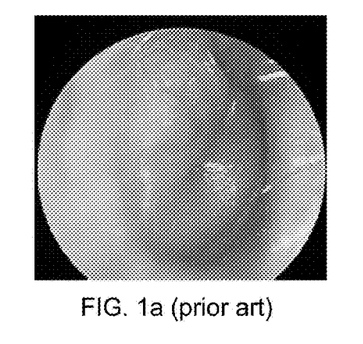
FIGS. 1a-c (prior art) are example images showing different conditions of the ear as well as features to distinguish the conditions.
Figure 1B:
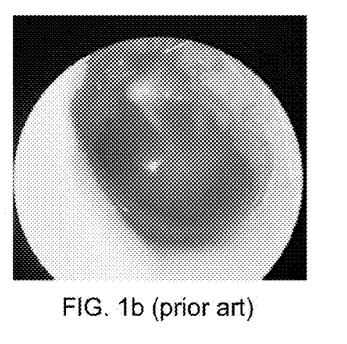
Figure 1C:
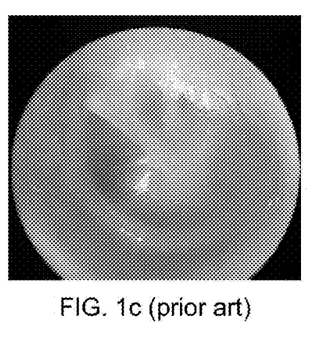

FIGS. 1a-c (prior art) are example images showing different conditions of the ear as well as features to distinguish the conditions. The three conditions shown are acute otitis media (AOM) in FIG. 1a, otitis media with effusion (OME) in FIG. 1b, and otitis media with no effusion (NOE) in FIG. 1c. Table 1 lists some features distinguishing the conditions. More specifically, Table 1 lists otoscopic findings on tympanic membrane (TM) images associated with the above three conditions.

TABLE 1

Otoscopic findings associated with clinical diagnostic categories on TM images

| | AOM | OME | NOE |
|---|---|---|---|
| Color | White, pale yellow, markedly red | White, amber, gray, blue | Gray, pink |
| Position | Distinctly full, bulging | Neutral, retracted | Neutral, retracted |
| Translucency | Opacified | Opacified, semi-opacified | Translucent |

As can be seen from FIGS. 1a-c and Table 1, the three conditions of the ear are different and they can be distinguished from one another based on one or more of the following features: color, position (e.g., 3D shape), and translucency. In order to make correct diagnosis of the ear condition, otoscopic images capturing accurate information about color, 3D shape and translucency of an inside of an ear (e.g., a tympanic membrane in an ear canal) are desirable.

Figure 2:
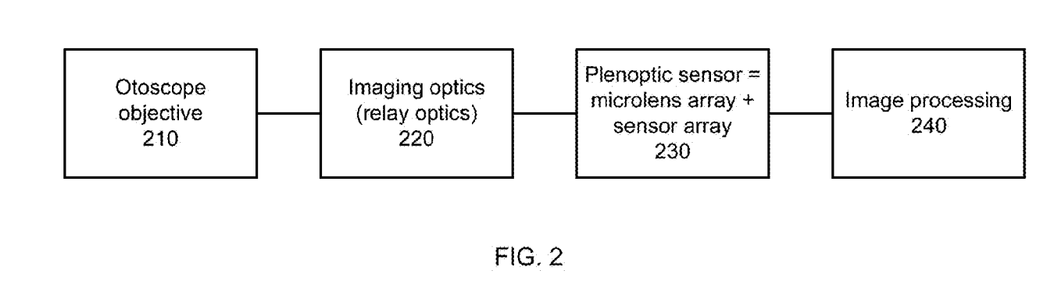
FIG. 2 is a block diagram of a plenoptic digital otoscope system.

FIG. 2 is a block diagram of a plenoptic digital otoscope system. The system includes an otoscope objective 210, imaging optics (relay optics) 220, a plenoptic sensor 230 and image processing 240. The otoscope objective 210 can be an imaging objective, as used in conventional otoscopes. The imaging optics 220 works in conjunction with the otoscope objective 210 to form a conventional image within the otoscope instrument. Rather than a conventional sensor array capturing this image, a plenoptic sensor 230 captures the image. The plenoptic sensor 230 is a sensor array with a microimaging array (e.g., a microlens array or pinhole array) mounted in front of it. In addition, a filter module (not shown in FIG. 2) can be inserted at a pupil plane of the optical train (or at one of its conjugates) to allow spectral or other filtering of the light. The digital information extracted by the plenoptic sensor 230 is sent to a computing module 240 that performs the image processing of the plenoptic data. In this way, three-dimensional and/or spectral data can be extracted.

The plenoptic otoscope head can be mounted on top of a handle that houses an illumination source (e.g., portable system) or can be connected to an illumination source (e.g., wall-mounted system). Such an illumination source may be an LED light source, a standard white illumination source, etc. The illumination source may have polarization characteristics as well. For example, it may emit unpolarized, partially polarized, or completely polarized (e.g., TE, TM) light.

Figure 3:
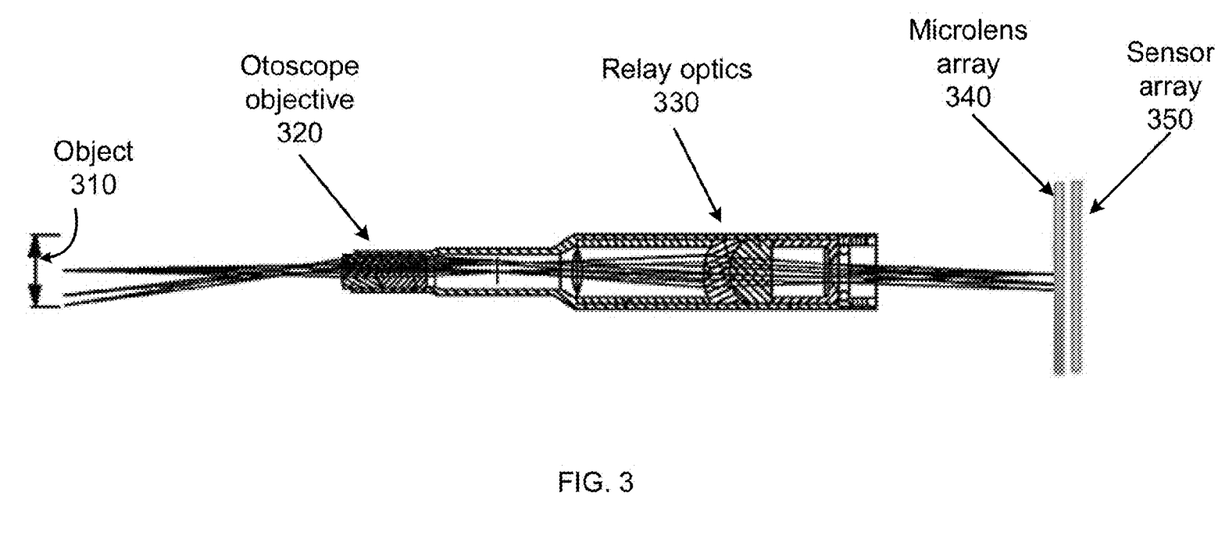
FIG. 3 shows an optical train of a plenoptic otoscope.

FIG. 3 shows an optical train of a plenoptic otoscope. The plenoptic otoscope includes two parts: a primary imaging system and a plenoptics sensor. The primary imaging system includes an otoscope objective 320 and relay optics 330. They cooperate to form a conventional image of an object 310 (e.g., an inside of an ear, a tympanic membrane, etc.). A plenoptic sensor (a microlens array 340 and a sensor array 350) is positioned so that the microlens array 340 is located in the conventional image plane, which is an intermediate image plane of the primary imaging system. The sensor array 350 then captures lightfield data, which will be referred to as the plenoptic image of the object 310.

In one embodiment, the plenoptic image contains depth data. A computing module (not shown in FIG. 3) further processes the captured plenoptic image to produce three-dimensional data. This operational mode of the plenoptic otoscope may be referred to as a depth imaging mode. For example, in the depth imaging mode, the plenoptic image captured by the sensor array 350 may be processed to provide a three-dimensional depth image of an inside of an ear.

Figure 4A:
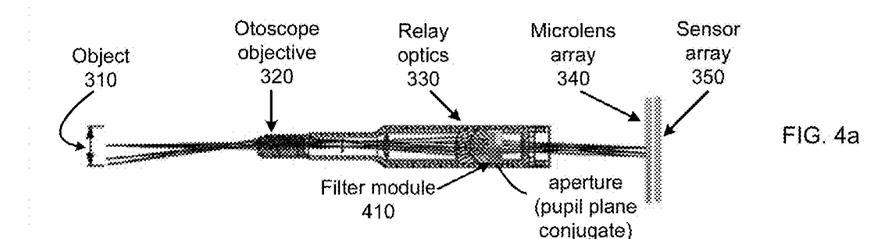
FIGS. 4a-c show optical trains of a plenoptic otoscope with filtering.
Figure 4B:
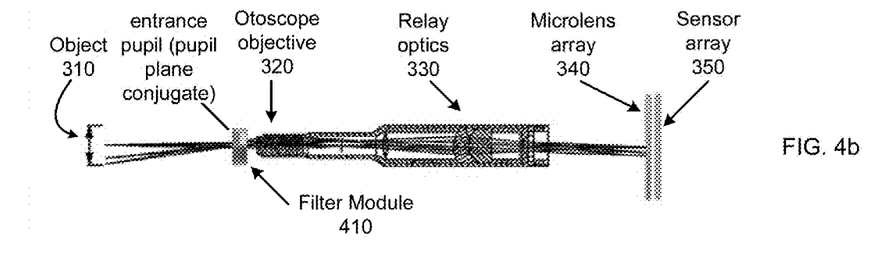
Figure 4C:
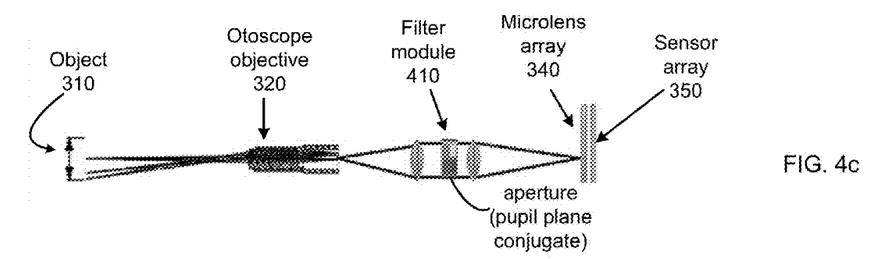

Another possible operational mode of the plenoptic otoscope is a spectral imaging mode. In the spectral imaging mode, the plenoptic image captured by the sensor array 350 contains spectral information and may be processed to provide two or more different spectral images of the object 310. In one embodiment, spectral imaging can be enabled by placing a filter module at a pupil plane conjugate of the plenoptic otoscope, as shown in FIGS. 4a-c. The term "pupil plane conjugate" is used to refer to any plane that is a pupil plane of the primary imaging system or a conjugate plane of that pupil plane. For example, the term pupil plane conjugate includes the entrance pupil plane and the exit pupil plane of the primary imaging system.

FIGS. 4a-c show different placements of the filter module. In FIG. 4a, the filter module 410 is located at an aperture between the relay optics and the plenoptic sensor. In FIG. 4b, the filter module 410 is located at the entrance pupil. In FIG. 4c, the filter module 410 is located at an aperture between a pair of relay lenses. In each of the embodiments shown in FIGS. 4a-c, the filter module 410 is positioned at a pupil plane conjugate.

In one implementation of FIG. 4b, the filter module is contained in a detachable tip (or ring), which is attached to the plenoptic otoscope. When the tip is attached, the filter module is positioned at the entrance pupil of the first lens group, as shown in FIG. 4b. As in a conventional otoscope, a speculum used to enter the ear canal may be attached to the detachable tip.

Figure 5A:
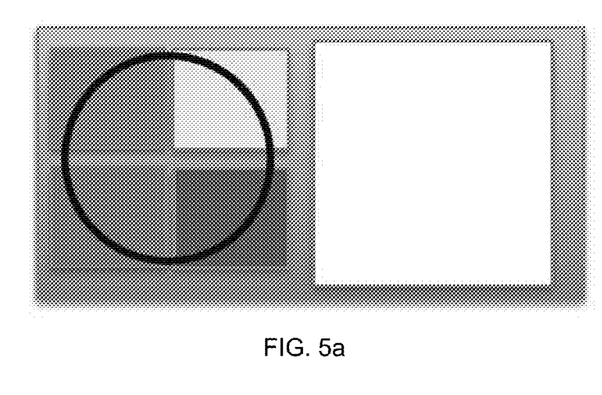
FIGS. 5a-b show use of a filter module with different spectral filters.
Figure 5B:
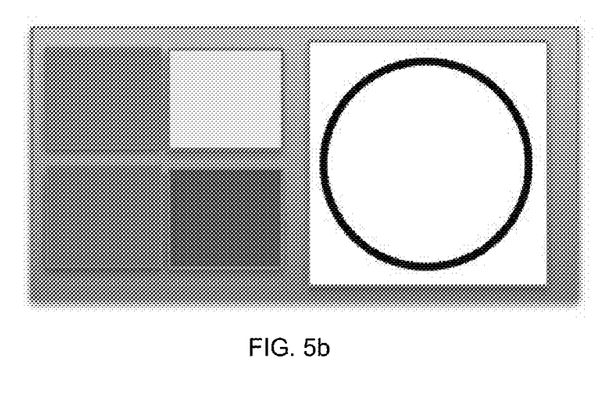

In one embodiment, the plenoptic otoscope is switchable between the depth imaging mode and the spectral imaging mode. In one approach, a clear filter is used for the depth imaging mode and one or more different spectral filters are used for the spectral imaging mode. To switch between the two modes, the filter module 410 could include one section that is clear and another section that contains the spectral filters. The filter module could be translated relative to the primary imaging system, so that the appropriate section is illuminated. An example of this type of filter module is shown in FIG. 5. This filter module could be positioned in a pupil plane conjugate and translated within the pupil plane conjugate to switch between the set of spectral filters and the clear filter. In FIG. 5, the black circle shows the cross-section of the light traveling through the otoscope.

In FIG. 5a, the light travels through the spectral filters, which are depicted as a red rectangle, a blue rectangle, a green rectangle, and a yellow rectangle. The portion of light that passes through a color filter forms an image of the object (within the plenoptic image) that has been filtered by the corresponding color filter. As a result, spectral imaging is enabled. In this example, a plenoptic image is formed, from which four different spectral images of the object (i.e., a red image, a blue image, a green image, and a yellow image) may be extracted.

In FIG. 5b, the filter module is translated relative to the primary imaging system so that the light travels through the clear aperture. This might be used for depth imaging, for example. In this example, a plenoptic image is formed, from which a three-dimensional depth image may be extracted.

This particular filter module has RGB filters for color imaging, plus a yellow filter since yellowish or amber color of tissue is an indicator, and is only shown as an example. In one embodiment, the filter module may include a plurality of different spectral filters. Filters having different colors and/or layouts may also be used in the filter module. For example, see U.S. patent application Ser. No. 13/040,809, filed on May 4, 2011, which is hereby incorporated by reference in its entirety.

Spectral imaging is useful to help distinguish different ear conditions. Some of the ear conditions are shown in FIGS. 1a-c and also in Table 1. For example, AOM is markedly red, OME features amber, and NOE contains gray and pink. In one embodiment, the filter module includes different filters selected to distinguish different ear conditions. Such a filter module is shown in FIGS. 5a-b, e.g., the filter module containing red-green-blue filters and a yellow filter.

Figure 6A:
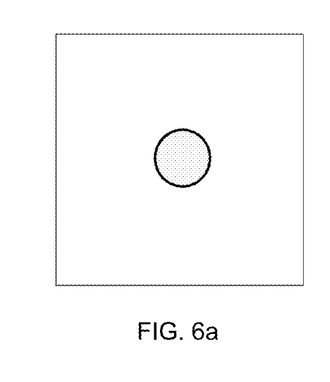
FIGS. 6a-c show additional filter modules.
Figure 6B:
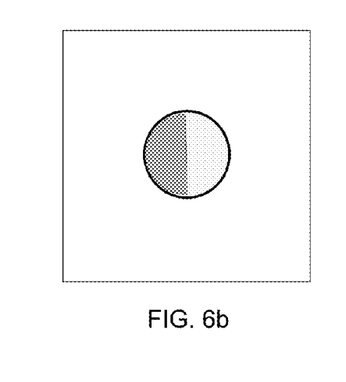

FIGS. 6a-c show some additional filter modules. In FIG. 6a, the filter module has a yellow filter and a transparent area. In FIG. 6b, the filter module has a yellow filter, an amber filter and a transparent area. The sensor array can also be fitted with spectral filters, such as a standard Bayer RGB pattern. Thus, when the filter modules in FIG. 6a or 6b are used with their transparent areas, the Bayer RGB pattern may be used to achieve color imaging. The yellow and amber filters in FIG. 6a and FIG. 6b can be used to extract extra color information. They can be used together with monochromatic sensors and/or RGB sensors (e.g., sensors fitted with a standard Bayer RGB pattern). Such extra color information (e.g., yellow, amber, etc.) can be used to distinguish different ear conditions.

Figure 6C:
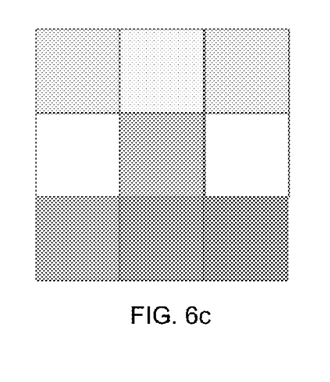

FIG. 6c has an array of filters. The center stripe includes three spectral filters: yellow, amber and a third spectral filter. These can be used for spectral imaging. The top right and top left filters are polarization filters, for example to reduce reflections. The polarization filters may also be useful in extracting illumination characteristics (e.g., when the illumination light has a certain degree of polarization). The middle right and middle left filters are transparent, for example for use in extracting depth information (e.g., depth imaging). The bottom right and bottom left filters are neutral density filters of different densities, for example to increase the dynamic range of the plenoptic otoscope.

Figure 7A:
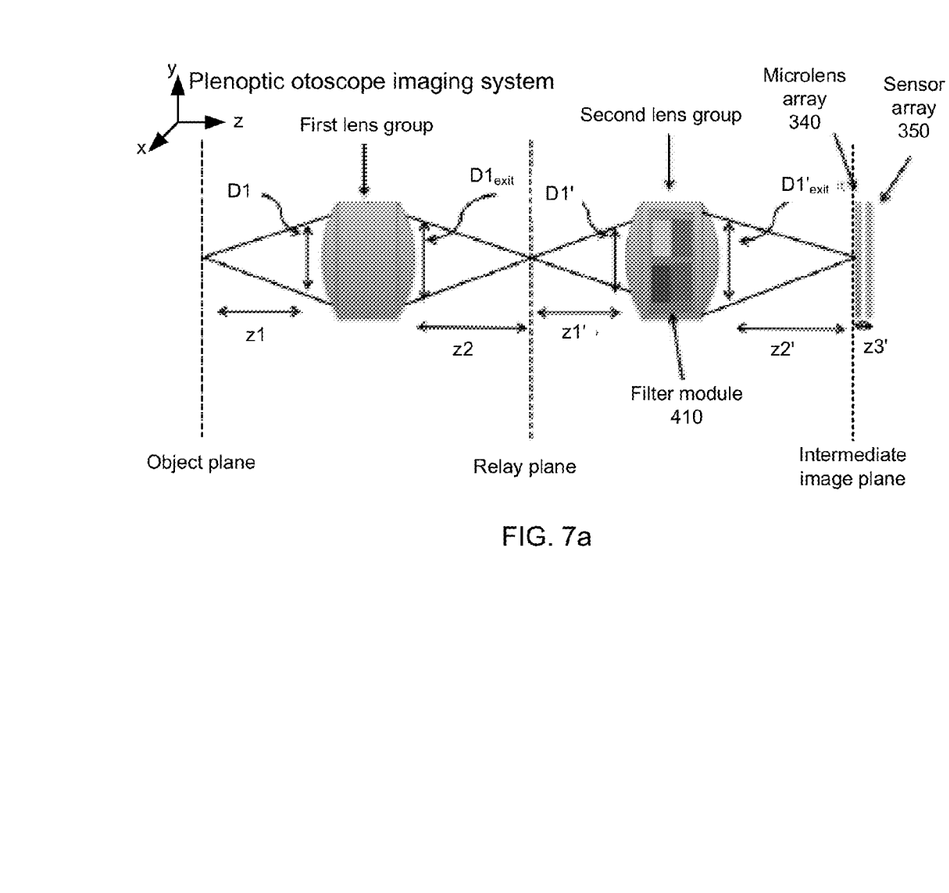
FIGS. 7a-b show a plenoptic otoscope system, introducing notations of dimensions.
Figure 7B:
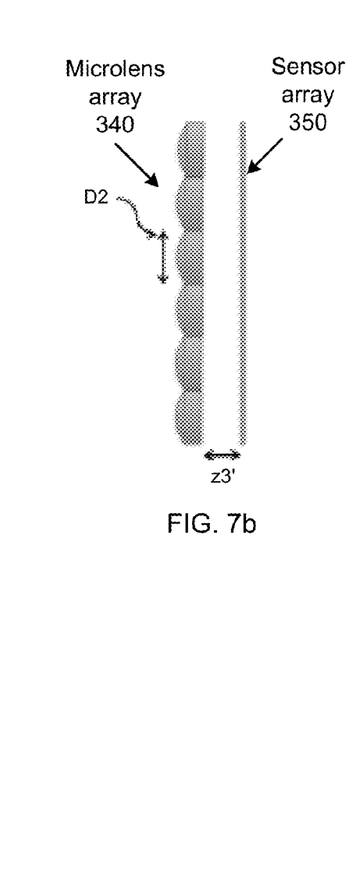

FIGS. 7a-b show a plenoptic otoscope system, introducing notation that will be used to describe different design considerations. FIG. 7a depicts a typical embodiment of a plenoptic otoscope, which includes a primary imaging system and a plenoptic sensor. The primary imaging system includes two lens groups. The first lens group is the otoscope objective, and the second lens group is the relay optics. The plenoptic sensor includes a microimaging array 340 and a sensor array 350. In FIG. 7b, the microimaging array is a microlens array 340, with each microlens having identical optical properties, such as diameter, radius of curvature, material, and thickness. In one embodiment, the diameter of a microlens is chosen to be between 10 and 100 micron.

As shown in FIG. 7a, the object (e.g., a tympanic membrane) is located in an object plane. It is imaged by the first lens group onto a first intermediate image plane (which may be referred to as the relay plane), and then imaged by the second lens group onto a second intermediate image plane where the microlens array 340 is positioned.

In many conventional otoscopes, the magnification of the primary imaging system is set such that the entire tympanic membrane (TM) can be imaged onto the sensor array 350 (as seen in FIGS. 1a-c). Suppose the sensor array 350 has a width W and a height H, and the diameter of the TM is h, then the magnification of the primary imaging system is given by M=min(W,H)/h, where min(x,y) returns the lesser value of x and y.

The average diameter for the TM of an adult is h=7 mm. Here we define optical system specifications for the example of a ⅓" sensor array with width W=4.6 mm and height H =3.7 mm. For this sensor array, the magnification for the primary imaging system is given by M =3.7 mm/7 mm=0.53. Such a magnification is typical for a conventional otoscope. In contrast, a microscope typically has a much larger magnification (>20), and a consumer camera imaging people or natural scenes typically has a much smaller magnification.

The total magnification of the primary imaging system is M=M1*M2, where M1 is the magnification of the first lens group, and M2 is the magnification of the second lens group. For illustration purposes, assume M2=1. In other approaches, M2 can be any suitable number other than 1. In the example where M2=1, M1=M. The working F-number, $N_w$, of the first lens group with magnification M is defined as $N_w$=(1+M)N, where N is the F-number of the primary imaging system (i.e., N=f/D1, where D1 is the diameter of the entrance pupil of the primary imaging system, and f is the effective focal length of the primary imaging system.). In one embodiment, the primary imaging system of the plenoptic otoscope is faster than F/8.

The working distance, z1, for the otoscope is the distance between the object and the first lens group. For imaging a TM, a typical working distance is 27-30 mm. The bones behind the TM are located approximately up to a distance of 15 mm from the TM. As a result, the working distance may vary, for example, from 27 mm up to 45 mm. For illustration purposes, assume the working distance z1=30 mm. The entrance pupil is located in the narrow tip of the otoscope close to the first lens group, and is generally smaller than the tip of the otoscope. The tip of an otoscope has a typical diameter of 4-5 mm in order to fit into an ear canal. Let's assume the entrance pupil to have a diameter of 2 mm. Then the effective focal length of the first lens group is f=N*D1=10.4 mm. The second lens group relays the image of the first lens group onto an intermediate image plane, where the microlens array 340 is positioned. The sensor array 350 is positioned at a distance z3' behind the microlens array 340 to capture the plenoptic image.

In one embodiment, the object is located near the hyperfocal distance of the first lens group. The hyperfocal distance is a distance beyond which all objects can be brought into an acceptable focus. Mathematically, the hyperfocal distance may be expressed as $p=f^2/(N c)+f$, where f is the effective focal length, N is the F-number, and c is the circle of confusion diameter limit. In one implementation, the numerical aperture of a microlens matches the image-side numerical aperture of the primary imaging system. That means the working F-number of the primary imaging system matches the F-number of the microlens. Furthermore, the distance z3' is chosen to be equal to the focal length of the microlens. In this configuration, the depth of field is bounded only in one direction, and therefore may be particularly suitable for imaging distant objects.

In one embodiment, the object is placed at a distance z1 away from the entrance pupil of the first lens group. The distance z2 between the exit pupil of the first lens group and the relay plane is determined by the lens equation as: $z2=1/(1/f1-1/z1)$, where f1 is the effective focal length of the first lens group.

The relationship between the first lens group and the second lens group is given by $D1_{exit}/D1'=z2/z1'$, where $D1_{exit}$ is the diameter of the exit pupil of the first lens group, D1' is the diameter of the entrance pupil of the second lens group, and z1' is the distance between the relay plane and the entrance pupil of the second lens group.

The distance z2' between the exit pupil of the second lens group and the intermediate image plane is determined by the lens equation as: $z2'=1/(1/f1'-1/z1')$, where f1' is the effective focal length of the second lens group.

The distance z3' between the microlens array and the sensor array is chosen such that $z3'=z2'\times M_{microlens}$. Here $M_{microlens}=D2/D1'_{exit}$ is the magnification of the microlens sub-system, where D2 is the diameter of the microlens (as shown in FIG. 7b) and $D1'_{exit}$ is the diameter of the exit pupil of the second lens group. This configuration is specific to imaging with a depth of field bounded in both directions, where the object may not be located near the hyperfocal distance. In comparison, a microscope typically has a much larger magnification (>20), a larger F-number (>15), and a much smaller working distance (a few millimeters).

In one embodiment, the filter module 410 is inserted at the aperture of the second lens group, as depicted in FIG. 7a. The filter module 410 is adjustable in such a way that it can be translated laterally in the x-y plane, which is perpendicular to the optical axis (z axis) of the second lens group. For clarity, the coordinate system is also shown in FIG. 7a. Furthermore, the second lens group may have a diaphragm/iris/shutter attached to the front/back of the filter module 410. This configuration may permit adjustment of the aperture diameter by opening and closing the diaphragm/iris/shutter.

Switching between depth imaging mode and spectral imaging mode may be accompanied by a change in the depth of field for the primary imaging system (in addition to changing filters). One way to change the depth of field is by adjusting the aperture size. For example, a larger aperture results in a shorter depth of field, which may benefit depth imaging due to the finer depth resolution. On the other hand, a smaller aperture results in a longer depth of field, which may be unsuitable for depth imaging but appropriate for spectral imaging.

In one embodiment, switching between depth and spectral imaging includes opening and closing the diaphragm/iris/shutter at the aperture plane of the second lens group. Two example configurations are given below. In the first configuration, with the effective focal length f=10 mm and a circle of confusion diameter of 0.019 mm, the aperture is wide open to enable a small F-number (e.g., F/5) and a small depth of field (<2 mm). This configuration is suitable for depth imaging or perhaps for combined depth+spectral imaging. In the second configuration, with the effective focal length f=10 mm and a circle of confusion diameter of 0.019 mm, the aperture is stopped down to enable a large F-number (e.g., F/16) and a large depth of field (>3.5 mm). This configuration may be suitable for spectral imaging only.

Switching between depth imaging mode and spectral imaging mode may also be accompanied by a change in focus for the primary imaging system. This may be done via a focusing mechanism. Such a focusing mechanism (e.g., a focusing ring) may move lenses in the primary imaging system and/or move the plenoptic sensor, so that objects at various distances can be focused onto the microlens array plane (i.e., the intermediate image plane). In one approach, the focusing mechanism is adjusted such that a region between 4-5 mm in front of the TM and up to 15 mm behind the TM can be imaged in focus onto the microlens array plane. This may enable different combinations of spectral and/or depth imaging at different regions of interest. For example, it may be desirable to have both depth and spectral imaging for a region near the TM (e.g., to fully distinguish the different ear conditions), while spectral imaging may be enough for other regions. By adjusting the focus, it is possible to select which portion of the ear canal should "receive more attention." For instance, one can adjust the focus with a fine step size (i.e., a fine depth resolution) near the TM to increase the 3D depth information for that region of interest, and adjust the focus with a coarse step size for other regions of the ear canal.

In one embodiment, the plenoptic otoscope is in the spectral imaging mode when the primary imaging system has a depth of field>5 mm. This is useful, for example, for imaging both the TM and the bones behind the TM in focus onto the microlens array plane. Conversely, the plenoptic otoscope is in the depth imaging mode when the primary imaging system has a depth of field<5 mm. In this mode, depth estimation of the TM is possible, for example, by focusing on the bones behind the TM and/or the narrow part of the ear canal in front of the TM. Illustratively, the first lens group may have a working distance up to 45 mm (about 15 mm behind the TM).

Figure 8A:
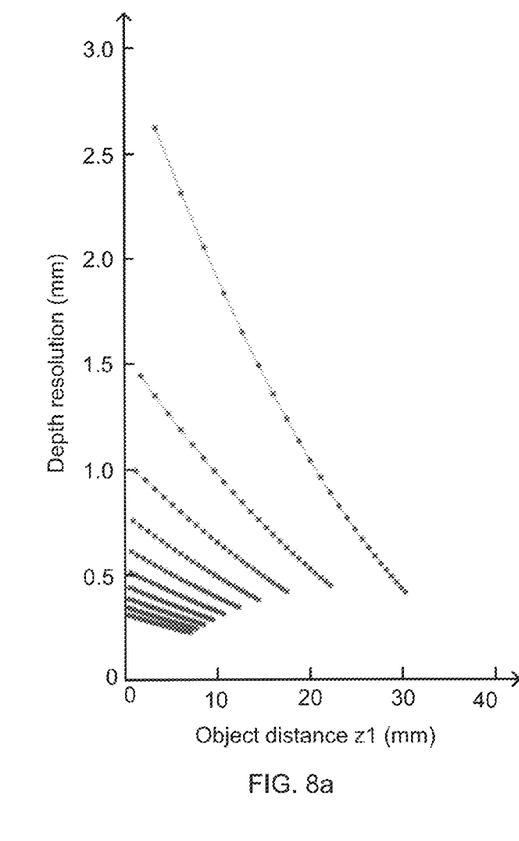
FIGS. 8a-b show simulation results for depth estimation using the Adelson/Wang model for a plenoptic otoscope.
Figure 8B:
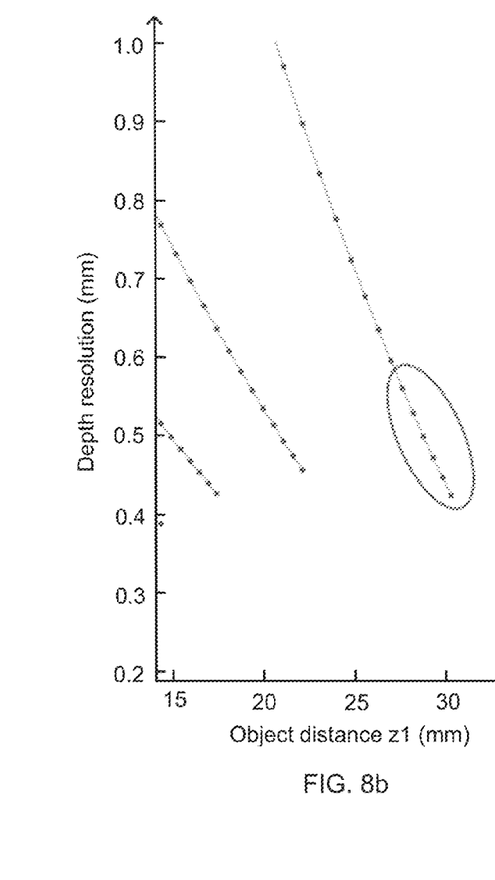

FIGS. 8a-b show simulation results for depth estimation using the Adelson/Wang model for a plenoptic otoscope in the depth imaging mode. The x-axis shows the object distance z1 in mm. The object is a point on the optical axis. The y-axis shows the depth resolution for that object point as calculated with Adelson/Wang's model. Each curve corresponds to a pair of lenslets with the lenslets above and below the optical axis at equal distance. Each dot on a curve corresponds to the depth resolution achieved when calculating the depth of an object from a given sensor point location under the lenslet pairs. In the figure, each curve has values calculated for 25 sensor point locations (25 locations in the upper half of the top lenslet, lower half of the bottom lenslet in the lenslet pair). Since the lenslet diameter=100 micron on pixel size 2 micron, we obtain 100/(2*2) pixel locations. These pairs of sensor locations in the two lenslets correspond to two different views of the object. FIG. 8b shows that from sensor point locations 1-6 under the first lenslet pair directly above and below the optical axis it is possible to calculate depth for an object at 30 mm at 0.5 mm depth resolution. The plenoptic otoscope has the following parameters: f=10 mm, F/8, z1=45 mm (focusing on the far end bone behind the ear drum), sensor pixel size=2 μm, microlens diameter D2=100 μm. The TM is approximately located at z1=30 mm. A bulged TM is visible between z1=27 mm and z1=30 mm. The depth resolution around the location of the TM (i.e., z1=30 mm) is predicted to be approximately 0.5 mm.

The diameter of the microlens is chosen such that at least 2 view pairs are available for depth estimation at a working distance of 30 mm. Depth estimation is possible from approximately 6 different view pairs of the plenoptic data.

FIG. 8b is a close-up of FIG. 8a, showing the 6 view pairs (circled in FIG. 8b) that are suitable for depth measurements of the TM.

In a plenoptic otoscope, it is also possible to include a view finder to enable the examiner to view an image through the view finder of the otoscope at the time of image capture. A beam splitter or a single lens reflex can be used to split the optical path and direct the image to the plenoptic sensor and to the view finder. For example, either a single lens reflex or a beam splitter may be inserted at the relay plane between the first lens group and the second lens group of an otoscope (as shown in FIG. 7a) to allow a medical expert to look at an ear drum, while the plenoptic image of the ear drum is captured on the sensor array of the same otoscope.

In other embodiments, a plenoptic otoscope system may include a set of detachable tips. Each detachable tip includes a different filter module. Each filter module may be used for a different purpose. For example, one filter module may be used for spectral imaging, while another filter module may be used for depth imaging. These detachable tips can be exchanged with one another, and are also referred to interchangeable tips. When a detachable tip is attached to the otoscope, the filter module included in that detachable tip is positioned at the entrance pupil of the primary imaging system.

The plenoptic otoscopes described can be designed and manufactured as original plenoptic instruments. Alternately, existing otoscopes can be modified to become plenoptic. In one embodiment, an after-market plenoptic conversion kit may be used to convert a conventional digital otoscope to a plenoptic digital otoscope. The conversion kit includes a plenoptic sensor with a microimaging array and a sensor array. The digital otoscope is equipped with a conventional sensor. During the conversion, the plenoptic sensor replaces the conventional sensor, such that the microimaging array (e.g., a microlens array or a pinhole array) is positioned at an image plane of the digital otoscope. For example, the microimaging array may be positioned at the plane where the conventional sensor was previously located.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A plenoptic otoscope comprising:
    a primary imaging system comprising an otoscope objective and relay optics cooperating to form an image of an inside of an ear at an intermediate image plane, the primary imaging system characterized by a pupil plane;
    a plenoptic sensor comprising a microimaging array and a sensor array, the microimaging array positioned at the intermediate image plane and the sensor array positioned at a first pupil plane conjugate; and
    a filter module positioned at a second pupil plane conjugate, the filter module comprising at least two different spectral filters, each spectral filter covering a different portion of the second pupil plane conjugate, wherein light that forms the image of the inside of the ear passes through the at least two different spectral filters.

2. The plenoptic otoscope of claim 1 further comprising:
    a detachable tip, the filter module located in the detachable tip and positioned at an entrance pupil of the primary imaging system when the detachable tip is attached to the otoscope.

3. The plenoptic otoscope of claim 1 further comprising:
    a set of detachable tips, each detachable tip including a different filter module, wherein the filter module is positioned at an entrance pupil of the primary imaging system when the detachable tip is attached to the otoscope.

4. The plenoptic otoscope of claim 1 wherein the filter module comprises a plurality of different filters selected to distinguish different ear conditions.

5. The plenoptic otoscope of claim 1 wherein the filter module is translatable relative to the primary imaging system.

6. The plenoptic otoscope of claim 1 wherein the otoscope is operable in a depth imaging mode, in which the sensor array captures a plenoptic image that is suitable to be processed to provide a three-dimensional depth image of the inside of the ear.

7. The plenoptic otoscope of claim 1 wherein the otoscope is operable in a spectral imaging mode, in which the sensor array captures a plenoptic image that is suitable to be processed to provide two or more different spectral images of the inside of the ear.

8. The plenoptic otoscope of claim 1 wherein the otoscope is switchable between a depth imaging mode and a spectral imaging mode.

9. The plenoptic otoscope of claim 8 wherein switching between the depth imaging mode and the spectral imaging mode comprises changing a depth of field for the primary imaging system.

10. The plenoptic otoscope of claim 9 wherein the depth of field is less than 5 mm when the otoscope is in the depth imaging mode, and the depth of field is greater than 5 mm when the otoscope is in the spectral imaging mode.

11. The plenoptic otoscope of claim 8 wherein switching between the depth imaging mode and the spectral imaging mode comprises changing a focus for the primary imaging system.

12. The plenoptic otoscope of claim 8:
    wherein the filter module comprises a plurality of different spectral filters and a clear filter, and the filter module is translatable relative to the primary imaging system;
    wherein switching between the depth imaging mode and the spectral imaging mode comprises translating the filter module so that the clear filter is illuminated when the otoscope is used in the depth imaging mode and the spectral filters are illuminated when the otoscope is used in the spectral imaging mode.

13. The plenoptic otoscope of claim 1 further comprising:
    a viewfinder coupled to the primary imaging system.

14. The plenoptic otoscope of claim 1 wherein the microimaging array is a microlens array.

15. The plenoptic otoscope of claim 1 wherein the microimaging array is a microlens array with microlenses having a diameter between 10 and 100 µm.

16. The plenoptic otoscope of claim 1 wherein the primary imaging system includes an aperture that is sufficiently large that the primary imaging system has an F-number that is not greater than F/8.

17. An after-market plenoptic conversion kit for use with a digital otoscope having a sensor, the digital otoscope characterized by a pupil plane and an image plane, the kit comprising:
- a plenoptic sensor comprising a microimaging array and a sensor array, the plenoptic sensor attachable to the digital otoscope to replace the sensor in the digital otoscope, the microimaging array positioned at the image plane of the digital otoscope and the sensor array positioned at a first pupil plane conjugate of the digital otoscope when the after-market plenoptic conversion kit is attached to the digital otoscope; and
- a filter module positioned at a second pupil plane conjugate of the digital otoscope when the after-market plenoptic conversion kit is attached to the digital otoscope, the filter module comprising at least two different spectral filters, each spectral filter covering a different portion of the second pupil plane conjugate, wherein light that forms the image of the inside of the ear passes through the at least two different spectral filters.

* * * * *